(12) United States Patent
Fu et al.

(10) Patent No.: US 7,754,944 B2
(45) Date of Patent: Jul. 13, 2010

(54) POLYNUCLEOTIDE CONSTRUCTS

(75) Inventors: Changlin Fu, Chesterfield, MO (US);
Brian Hauge, Wildwood, MO (US);
Vicky Gavrias, Defiance, MO (US)

(73) Assignee: Monsanto Technology LLC, St. Louis, MO (US)

( * ) Notice: Subject to any disclaimer, the term of this patent is extended or adjusted under 35 U.S.C. 154(b) by 442 days.

(21) Appl. No.: 11/695,108

(22) Filed: Apr. 2, 2007

(65) Prior Publication Data

US 2007/0234442 A1 Oct. 4, 2007

Related U.S. Application Data

(60) Provisional application No. 60/788,816, filed on Apr. 3, 2006.

(51) Int. Cl.
*C12N 15/84* (2006.01)
*C12N 15/65* (2006.01)
*C12N 15/66* (2006.01)
*C12N 5/04* (2006.01)
*C12N 5/10* (2006.01)
*A01H 5/00* (2006.01)
*A01H 5/10* (2006.01)

(52) U.S. Cl. .................. 800/294; 800/300; 435/91.2; 435/320.1; 435/419; 435/469; 536/24.1; 536/24.2

(58) Field of Classification Search .................. None
See application file for complete search history.

(56) References Cited

U.S. PATENT DOCUMENTS

| 5,137,814 | A | 8/1992 | Rashtchian et al. .......... 435/91 |
| 5,580,759 | A | 12/1996 | Yang et al. |
| 6,358,712 | B1 | 3/2002 | Jarrell et al. |
| 6,495,318 | B2 | 12/2002 | Harney |
| 2006/0147961 | A1 | 7/2006 | Dong et al. ................. 435/469 |

OTHER PUBLICATIONS

Hellens et al. Plant Molecular Biology 42: 819-832 (2000).*
Urwin et al. The Plant Journal 24(5): 583-589 (2000).*
Aslanidis et al., "Ligation-independent cloning of PCR products (LIC-PCR)," *Nucleic Acids Research*, 18(20):6069-6074, 1990.
Rashtchian et al., "Uracil DNA Glycosylase-mediated cloning of PCR-amplified DNA: Application to Genomic and cDNA cloning." Analytical Biochemistry 206:91-97. 2002.
Coljee et al., "Seamless gene engineering using RNA- and DNA-overhang cloning." Nature Biotechnology 18:789-791. 2000.
Donahue et al., "Rapic gene cloning using terminator primers and modular vectors." Nucleic Acids Research 30(18):30-35. 2002.
Li et al., "Ligation independent cloning irrespective of restriction site compatibility." Nucleic Acids Research 25(20):4165-4166. 1997.
Newton et al., "The production of PCR products with 5' single-stranded tails using primers that incorporate novel phosphoramidite intermediates." NucAcidsRsch 21(5):1155-1162, (1993).
Endy et al., "Foundations for engineering biology." Nature 438(24):449-453. 2005.

* cited by examiner

*Primary Examiner*—David T Fox
(74) *Attorney, Agent, or Firm*—Thomas P. McBride, Esq.; Sonnenschein Nath & Rosenthal LLP

(57) ABSTRACT

Synthetic modular polynucleotide constructs are useful for gene expression in plants, methods for making and using such constructs, and plants transformed with such constructs. The constructs comprise unique restriction sites for each modular element and may further comprise polynucleotide identifier sequences.

18 Claims, No Drawings

US 7,754,944 B2

POLYNUCLEOTIDE CONSTRUCTS

This application claims benefit under 35USC §119(e) of U.S. provisional application Ser. No. 60/788,816 filed Apr. 3, 2006, herein incorporated by reference in its entirety.

FIELD OF THE INVENTION

Disclosed herein are polynucleotide constructs of modular elements useful in transgenic plant cells, plants and seeds and methods of making and using such constructs, plant cells, plants and seeds.

BACKGROUND OF THE INVENTION

The tools of molecular biology have enabled researchers to introduce segments of DNA from one organism into another organism. As the need for the introduction of multiple segments of DNA and larger fragments of DNA into numerous target hosts increases, the need for novel cloning strategies and improved vector constructs increases accordingly.

Vectors for *Agrobacterium*-mediated transformation of plant cells typically comprise restriction cloning sites, T-DNA border elements from the tumor-inducing plasmid of *Agrobacterium tumefaciens*, a gene of interest, some type of selectable marker, and at least one bacterial origin of replication. These vectors are then introduced into plant cells to transform them with the gene of interest.

There is a need in the art for vectors that are relatively small for convenience of manipulation and capable of prolific replication in a living cell enabling the amplification of the inserted donor DNA. There is also need in the art for vectors with convenient restriction sites that can be used for insertion of the DNA to be cloned. It is also desirable that there be a mechanism for easy identification, recovery and sequencing of the recombinant molecule.

It is common to develop plant transformation vectors from earlier-used vectors with the result that vector constructs typically contain unwanted or unneeded restriction sites and unnecessarily large stretches of polynucleotide that serve no purpose other than to link essential modular elements of a construct.

As plant transformation becomes more widely used, especially in high throughput screening of transgenic constructs, there is an increased need for technology to track both specific vector constructs and general transformation events during all stages of development, i.e. from the cloning of a single bacterial cell with a gene of agronomic interest, through the testing of a seed of a fertile transgenic plant that may eventually contain the vector construct for both quality control and regulatory purposes.

SUMMARY OF THE INVENTION

This invention provides polynucleotide constructs, suitable for plant transformation, that comprise modular elements. Modular elements in such constructs comprise elements to facilitate transformation such as T-DNA orders, elements to facilitate replication such as origins of replication, transcription units such as marker transcription units and units for expressing functional RNA in plant cells. Sub elements are likewise modular, e.g. transcription regulatory elements such as promoters, transit peptide DNA and polyadenylation segments that are operably linked to transcribable DNA which encodes functional RNA. The modular elements and sub elements are each flanked by a unique pair of restriction sites. Such modular elements are easily inserted or replaced in a construct increasing the utility of a construct for future modification. In one aspect of the invention the construct comprises stop codons in all six reading frames (upper and lower strands) flanking the left- and right-border sequences, preventing translational read-through.

In another aspect of the invention, the construct comprises a unique polynucleotide sequence which allows for the identification of the construct and any cell into which the construct is transformed. In another aspect, the invention provides for a construct comprising a unique polynucleotide identifier comprising a sequence of at least 9 nucleotide base pairs, preferably consisting of the nucleotides adenine, guanine and cytosine to avoid unintended transcription start sites and preferably located adjacent to an transcription unit to be inserted into a plant cell.

This invention also provides transgenic plant cells, fertile plant and seed comprising such polynucleotide constructs, and methods of screening a plurality of transgenic plants incorporating various embodiments of such constructs.

DETAILED DESCRIPTION OF THE INVENTION

"Polynucleotide" means a polymer of nucleic acids.

"Transcribable DNA" means a DNA molecule capable of being transcribed into a RNA molecule including, but not limited to, RNA that is translatable to a protein or polypeptide and RNA that is useful for gene suppression.

As used herein, the term "operably linked" refers to sub elements that function together in a transcription unit, e.g. the linkage of regulatory elements such as a promoter DNA molecule, a transit peptide DNA molecule and a polyadenylation DNA molecule to transcribable DNA in a manner that the transcribable DNA is readily transcribed in a transgenic plant cell.

"T-DNA" means transfer-DNA which integrates into a genome. For *Agrobacterium*-mediated transformation T-DNA is typically flanked by T-DNA borders isolated from a disarmed tumor-inducing plasmid of *Agrobacterium tumefaciens*

"Backbone" means, with respect to a plasmid for transformation, the elements of a plasmid that are typically used for maintenance and replication of the plasmid and that are separated from intended T-DNA. In the case of plasmids for *Agrobacterium*-mediated transformation, the backbone typically comprises origins of replication and selectable markers for use in a host cell. Useful backbone elements for plasmid constructs designed for *Agrobacterium*-mediated plant transformation are *Escherichia coli* origin of replication such as ori322 and the Spec/Strp selectable marker that expresses Tn7 aminoglycoside adenyltransferase (aadA) conferring resistance to spectinomycin or streptomycin. In certain aspects of the invention the backbone is reduced to a minimal size, e.g. not greater than about 3500 base pairs of nucleotides.

"Modular" refers to elements in a DNA construct that can be readily removed from the construct. For example, modular elements in a construct have unique pairs of restriction sites flanking each element within the construct, enabling the exclusive manipulation of individual elements.

"Construct" means an engineered polynucleotide molecule, e.g. a plasmid.

"Vector" means a construct designed for the introduction of heterologous DNA into a host cell.

Methods for preparing polynucleotide constructs have been well known in the art for more than 20 years and are routinely practiced in laboratories worldwide using common enzymes such as restriction endonucleases and ligases.

Ligase independent cloning methods are also useful, see U.S. patent application Ser. No. 11/298,234. See also Aslanidis and de Jong, Nucleic Acids Research, 18 (20), pages 6069-6074 (1990); U.S. Pat. No. 5,580,759 (Yang et al.); U.S. Pat. No. 5,137,814 (Rashtchian et al.) and U.S. Pat. No. 6,495,318 (Harney), all of which are incorporated herein by reference.

Certain embodiments of the constructs of this invention comprise DNA that functions as a polynucleotide identifier sequence which is useful for characterization of transformed plant cells, plants, and seeds at the molecular level, e.g. by providing information about the composition and integrity of the inserted DNA, the number of copies of the inserted DNA, the number of sites of insertion, as well as provides a mechanism of tracking specific transformation events throughout the development of a commercial product. DNA that functions as polynucleotide identifier sequences in the constructs of this invention comprise nucleotides in a randomly-generated polynucleotide sequence that are screened for lack of start codons as well as screened for lack of 100% identity to a polynucleotide sequence in the genome of organisms selected from a group of the kingdoms consisting of: Archaebacteria, Monera, Protista, Fungi, Plantae, Animalia. The DNA that functions as a polynucleotide identifier sequence comprises flanking segments that serves as bybridization sites for PCR primers and, optionally, internal segments that serve as hybridization sites for PCR amplification of separate identifying components.

Methods are well known in the art for transforming plant cells. For instance, *Agrobacterium*-mediated transformation is described in U.S. Pat. No. 5,159,135 (cotton); U.S. Pat. No. 5,824,877 (soybean); U.S. Pat. No. 5,591,616 (corn); and U.S. Pat. No. 6,384,301 (soybean), all of which are incorporated herein by reference. Plant cells that survive exposure to a selective agent, or plant cells that have been scored positive in a screening assay are indicated as being transformed. Such cells can be cultured in regeneration media and allowed to mature into plants. Developing plantlets regenerated from transformed plant cells can be transferred to plant growth mix, and hardened off, for example, in an environmentally controlled chamber at about 85% relative humidity, 600 ppm $CO_2$, and 25-250 microeinsteins $m^{-2}s^{-1}$ of light, prior to transfer to a greenhouse or growth chamber for maturation. Plants are regenerated from about 6 weeks to 10 months after a transformant is identified, depending on the initial tissue. Plants may be pollinated using conventional plant breeding methods known to those of skill in the art and seed produced, for example self-pollination is commonly used with transgenic corn. The regenerated transformed plant or its progeny seed or plants can be tested for expression of the recombinant DNA and selected for the presence of enhanced agronomic trait.

Transgenic plants derived from the transgenic plant cells are grown to generate transgenic plants and can be screened for having an agronomic trait of interest imparted by transcribed DNA as compared to a control plant.

Thus a method of this invention is the facilitated high throughput screening of such transgenic plants or progeny seed using multiple constructs having diverse transcribable DNA. Such plants or progeny seed with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seed provided herein demonstrate improved agronomic traits that contribute to increased yield or other trait that provides increased plant value, including, for example, improved seed quality.

The following examples are included to illustrate embodiments of the invention.

EXAMPLE 1

This example illustrates the fabrication of polynucleotide constructs useful for *Agrobacterium*-mediated transformation of a corn plant where the construct is a vector comprising as intended T-DNA a marker transcription unit and an exogenous protein transcription unit and as backbone origins of replication and a selectable maker transcription unit.

A base plasmid (construct 1) is constructed with the following elements:

1—left border from *A. tumefaciens* tumor-inducing plasmid

2—plant selectable marker transcription unit with operably linked sub elements:
   a. CaMV35S promoter
   b. DNA coding an EPSP synthase
   c. *A. tumefaciens* NOS 3' polyadenylation segment 3—protein expression transcription unit with operably linked sub elements
   a. rice actin 1 promoter
   b. DNA coding a *B. subtilis* cold shock protein B
   c. rice actin 1 polyadenylation segment 4—right border from *A. tumefaciens* tumor-inducing plasmid 5—*E. coli* origin of replication 6—*A. tumefaciens* origin of replication 7—marker transcription unit for selection by spectromycin/streptomycin resistance In the plasmid construct there is a unique pair of restriction sites flanking each of the identified elements and sub elements. The backbone elements, 5, 6 and 7 comprise fewer than 3500 nucleotides.

An additional plasmid (construct 2) is prepared by removing element 3 (the plant selectable marker transcription unit) from construct 1 and inserting a new plant selectable marker transcription unit which expresses a protein imparting resistance to glufosinate herbicide.

An additional plasmid (construct 3) is prepared by removing the sub element 3.b. (the DNA coding an EPSP synthase) from element 3 of construct 1 and inserting a new DNA coding an dicamba monooxygenase so that the plant selectable marker transcription unit imparts resistance to dicamba.

An additional plasmid (construct 4) is prepared by removing element 4 (the protein expression transcription unit) from construct 1 and inserting a new gene suppression transcription unit which expresses double stranded RNA for suppressing a native corn gene encoding for lysine ketoglutarate reductase.

An additional plasmid (construct 5) is prepared by inserting into construct 1 DNA comprising a set of stop codons in all three reading frames on the sense strand and a set of stop codons in all three reading frames on the antisense strand between left border (element 1) and the plant marker transcription unit (element 2) and between the protein expression transcription unit (element 3) and the right border (element 4).

An additional plasmid (construct 6) is prepared by inserting into construct 1 DNA that functions as polynucleotide identifier sequence between the polyadenylation segment (sub element 3.c.) and the right border (element 4). The DNA that functions as polynucleotide identifier sequence serves as a genetic barcode and comprises nucleotides designed with the following sequence:

(a) a sequence for designing a forward PCR primer,
(b) a sequence of nine nucleotides for a first tag that is useful for identifying a project in which the construct is being used,
(c) a sequence for designing a first reverse PCR primer,
(d) a sequence of nine nucleotides for a second tag that is useful for identifying the specific construct used in a project,
(e) a sequence for designing a second reverse PCR primer.

PCR amplification using a primer pair designed as the forward primer and first reverse primer amplifies the DNA of the first tag. PCR amplification using a primer pair designed as the forward primer and second reverse primer amplifies the DNA of the second tag. The primer pairs have a melting temperature greater than 45 degrees Celsius.

EXAMPLE 2

This example illustrates the preparation of transgenic plant cells and progeny transgenic plants and seeds using polynucleotide constructs of this invention.

Each of the constructs prepared in Example 1 is transformed into corn callus by *Agrobacterium*-mediated transformation. Transformed calli were regenerated into plants, transferred to soil, and grown to produce progeny seed.

Analysis of the transformation efficacy of the constructs of this invention showed that there is no statistically significant difference in the performance of a polynucleotide construct of this invention as compared to a high performance construct according to prior art practice.

EXAMPLE 3

This example illustrates the advantages of the polynucleotide constructs of this invention in high throughput screening. Additional constructs are prepared by modifying construct 5 of Example 1 by specifically replacing the promoter of sub element 3.a. and the transcribable DNA of sub element 3.b. with the promoters and transcribable DNA shown in the following tables and by replacing the DNA that functions as a polynucleotide identifier sequence with a unique sequence of nine nucleotides for a second tag. Constructs with each of the 28 combinations of promoter and transcribable DNA also have DNA that functions as a unique polynucleotide identifier. At least 10 events of transgenic corn cells are prepared using each of the 28 combinations. Transgenic corn plants are regenerated and grown to mature plants in a greenhouse with other transgenic corn plants all of which are evaluated in a plurality of screens to identify plants having an enhanced agronomic trait. The source DNA providing the enhanced agronomic trait is identified by analysis of the DNA amplified by PCR from the first and second tags

| Promoter | Source gene | reference. |
|---|---|---|
| 1 | maize napin | U.S. Pat. No. 5,420,034 |
| 2 | maize glutelin1 | Russell et al. (1997) Transgenic Res. 6(2): 157-166 |
| 3 | maize L3 oleosin | U.S. Pat. No. 6,433,252 |
| 4 | maize globulin 1 | Belanger et al (1991) Genetics 129: 863-872. |
| 5 | *Arabidopsis thaliana* (Rubisco) small subunit | Fischhoff et al. (1992) Plant Mol Biol. 20: 81-93 |
| 6 | pyruvate orthophosphate dikinase (PPDK) | Taniguchi et al. (2000) Plant Cell Physiol. 41(1): 42-48. |
| 7 | rice actin 1 promoter with a rice actin 1 intron enhancer | U.S. Pat. No. 5,641,876 |

| Transcribable DNA | Encoded protein | reference |
|---|---|---|
| A | Sucrose Phosphate Synthase | Planta (2001) 212: 817-822 and numerous external and internal reports |
| B | Asparagine synthetase | Lam et al. (2003). Plant Physiol. 132, 926-935 |
| C | ANT | US patent application publication 2002/0170093 A1 |
| D | plant hemoglobin genes | Plant Journal (2003) 35: 763-770 |

What is claimed is:

1. A polynucleotide construct, comprising as modular elements:
   a. one or more T-DNA border elements;
   b. a series of adjacent elements, said series not greater than 3500 nucleotide base pairs, said series comprising combinations of the following elements:
      i. one or more origin of replication elements, wherein each of said elements is selected for its ability to induce replication of a plasmid comprising said element; and
      ii. a marker transcription element, comprising a promoter linked to a transcribable DNA, that enables the identification or selection of a cell comprising said element;
   wherein each of said elements if flanked by a unique pair of restriction sites, by which each of said elements may be individually excised from the construct by restriction enzymes.

2. The construct of claim 1, produced by a method selected from the group consisting of: ligation independent cloning, polynucleotide synthesis, glycosylase-mediated cloning, directional cloning, overhang cloning, ordered gene assembly, cloning using terminator primers, PCR amplification of the entire vector followed by circularization, and PCR amplification of individual components that are each flanked by restriction sites followed by annealing.

3. The construct of claim 1, further comprising at least one transcription unit element for expressing RNA in transgenic plant cells, wherein said transcription unit element is flanked by a unique pair of restriction sites by which it can be individually excised from the construct by restriction enzymes.

4. The construct of claim 3, wherein said transcription unit element comprises as sub-elements:
   a. a promoter functional in a plant cell for transcribing RNA from an operably linked DNA sequence, and
   b. a transcribable DNA operably linked to, and heterologous with respect to, said promoter, wherein each sub-element is flanked by a unique pair of restriction sites, by which each of said sub-elements can be individually excised from the construct by restriction enzymes.

5. The construct of claim 4, further comprising a polynucleotide identifier sequence comprising at least 9 nucleotide base pairs.

6. The construct of claim 5 wherein said polynucleotide identifier sequence is randomly generated.

7. The construct of claim 5 wherein said polynucleotide identifier sequence is selected from a tabulated series of variants.

8. The construct of claim 5, wherein said polynucleotide identifier sequence in its sense strand consists of nucleotide bases selected from the group consisting of adenine, guanine and cytosine.

9. The construct of claim 5, wherein said polynucleotide identifier sequence is adjacent to a transcription unit element.

10. The construct of claim 3, wherein the T-DNA border elements comprise a left border element and a right border element separating said series of adjacent elements and said at least one transcription unit element.

11. The construct of claim 3, further comprising stop codons in all possible sense and anti-sense reading frames between said border elements and the transcription unit elements.

12. The construct of claim 1, wherein said origin of replication element(s) comprise a segment of DNA for replication of the plasmid in an *E. coli* bacterium and a segment of DNA for replication of the plasmid in an *Agrobacterium* bacterium.

13. The construct of claim 1, wherein said marker transcription unit element is a bacterial selectable marker.

14. The construct of claim 1, wherein the modular elements comprise in the following order:
   a. a T-DNA Right Border element;
   b. a set of stop codons in all three reading frames on the sense strand and a set of stop codons in all three reading frames on the antisense strand;
   c. at least one element for gene expression in plants in the form of a transcription unit cassette, comprising:
      i. a promoter functional in a plant cell for transcribing RNA from operably linked DNA,
      ii. a transcribable DNA sequence operably linked to said promoter; and
   d. at least one polynucleotide identifier sequence;
   e. a set of stop codons in all three reading frames on the sense strand and a set of stop codons in all three reading frames on the antisense strand;
   f. a T-DNA Left Border element; and
   g. a series of elements comprising:
      i. an origin of replication element comprising a segment of DNA for replication in *E. coli* and a segment of DNA for replication in at least one *Agrobacterium* species; and
      ii. a bacterial selectable marker.

15. A plant cell comprising the construct of claim 1.

16. A plant comprising the construct of claim 1.

17. A seed of the transgenic plant of claim 16, comprising said construct.

18. A method for screening a plurality of plants transformed with a construct of claim 1, comprising growing said plants under suitable condition and selecting for the tolerance conferred by said marker transcription unit element transcribable DNA.

* * * * *

UNITED STATES PATENT AND TRADEMARK OFFICE
CERTIFICATE OF CORRECTION

PATENT NO.         : 7,754,944 B2                                                  Page 1 of 1
APPLICATION NO.    : 11/695108
DATED              : July 13, 2010
INVENTOR(S)        : Fu et al.

It is certified that error appears in the above-identified patent and that said Letters Patent is hereby corrected as shown below:

In claim 1, column 6, line 53, delete "transcription element" and insert
--transcription unit element--.

In claim 1, column 6, line 57, delete "elements if" and insert --elements is--.

Signed and Sealed this

Fifth Day of October, 2010

David J. Kappos
*Director of the United States Patent and Trademark Office*